United States Patent [19]

Ser et al.

[11] Patent Number: 4,486,448

[45] Date of Patent: Dec. 4, 1984

[54] COPPER LANOLATE AND ANTI-ACNE COMPOSITIONS CONTAINING THE SAME FOR TOPICAL APPLICATION TO THE SKIN

[75] Inventors: Jean-Claude Ser, Chevilly Larue; Quang L. N'Guyen, Antony; Catherine Millet, Paris; Béla Szarazi, Brie, all of France

[73] Assignee: Societe Anonyme dite: L'Oreal, Paris, France

[21] Appl. No.: 434,186

[22] Filed: Oct. 14, 1982

[30] Foreign Application Priority Data

Oct. 20, 1981 [FR] France ............................ 81 19661

[51] Int. Cl.³ .................... A01N 55/02; C07F 1/08; A61K 31/30
[52] U.S. Cl. ............................ 424/294; 260/438.1; 424/318
[58] Field of Search ................. 260/414; 424/294, 318

[56] References Cited

U.S. PATENT DOCUMENTS

| | | | |
|---|---|---|---|
| 2,215,955 | 9/1940 | Cox | 260/414 X |
| 2,365,915 | 12/1944 | Taylor | 260/414 X |
| 3,701,729 | 10/1972 | Fischer | 260/414 X |
| 4,123,511 | 10/1978 | Heintze | 424/294 X |
| 4,177,288 | 12/1979 | Gohlke | 424/294 X |

*Primary Examiner*—Helen M. S. Sneed
*Attorney, Agent, or Firm*—Cushman, Darby & Cushman

[57] ABSTRACT

Copper lanolate, a novel product, can be produced by initially preparing an isotropic solution of a sodium or potassium salt of lanolic acid and thereafter precipitating copper lanolate therefrom by the addition thereto of a solution of a copper salt. The resulting copper lanolate is employed in anti-acne compositions for topical application to the skin.

19 Claims, No Drawings

COPPER LANOLATE AND ANTI-ACNE COMPOSITIONS CONTAINING THE SAME FOR TOPICAL APPLICATION TO THE SKIN

The present invention relates to a new copper-based organic compound as well as to cosmetic or therapeutic compositions containing this compound. More particularly, the present invention relates to an anti-acne composition containing copper lanolate.

Acne, which is associated most often with young people between the ages of about 14 to 30, has for its essential origin a hormonal disorder and is manifested by the appearance of pustules, pimples or black heads on the face, the neck and at times on the back and chest, the sebaceous glands being under the direct control of the endogenous hormonal system.

This manifestation of acne results from hyperkeratinization of the sebaceous gland ducts causing a narrowing of duct passages so that sebum does not freely flow out, thereby forming a favorable medium for bacteria growth.

The bacteria generally are not considered as playing an important role in the origin of acne but their importance is essentially due to the fact that they are susceptible of rupturing the sebaceous gland ducts, thereby releasing irritating fatty acids which cause local inflammation phenomena.

Since the origin of acne is partially hormonal, as this has been demonstrated, treatment of this disorder has, for a number of years, been based on the application of hormones (estrogens) although without significant success. Presently, this treatment involves a topical treatment of the lesions caused by acne.

Further, since acne produces a hypersecretion of the sebaceous glands, it has been proposed to employ substances having a sebo-regulating or sebo-inhibiting activity.

Among such substances are sulfur or certain sulfur compounds, organic or mineral, but their activity has not always been satisfactory or constant.

Additionally, there has been proposed the use of certain derivatives which act both on the keratinization process and the sebogenesis process. These derivatives include, for example, certain cysteine or cysteamine derivatives.

Since inflammation phenomenon is caused essentially by the presence of certain bacteria in the sebum, there has also been proposed the use of antiseptic agents, principally quaternary ammonium compounds, as well as chlorhexidine. However, these compounds have not been totally satisfactory especially since all are not active against the principal germs associated with acne, these germs being, essentially, *Staphylococcus aureus*, *Staphylococcus albus* and especially *Corynebacterium acnes* and *Propionibacterium granulosum*.

To effectively treat the manifestations of acne it is necessary that the active compounds be able to inhibit the lipolytic enzymes produced by these germs and principally by *Corynebacterium acnes* and *Propionibacterium granulosum* which are present on the surface of the skin and which are considered as being the principal agents responsible for the manifestations of acne.

In effect, by inhibiting the lipolytic enzymes, hydrolytic cleavage of the normal triglycerides of sebum is avoided thereby preventing the formation of long chain fatty acids, the presence of which causes typical inflammation phenomena of acne lesions.

As a result of a systematic study of numerous compounds, it has now been found, in a quite surprising manner, that copper lanolate is an excellent anti-acne agent especially with regard to the fact that it is quite active against the spectrum of principal germs associated with acne and especially against *Corynebacterium acnes* and *Propionibacterium granulosum*.

The tests carried out using this compound by the method of diffusion with tablets have permitted to verify and confirm this activity on these two principal germs of acne.

In addition to this anti-acne activity of copper lanolate, it has also noted that this non-toxic and slightly penetrating compound can be employed as a sun screen agent in combination with conventional sun screen agents such as, for example, benzylidene camphor or 2-ethyl-hexyl p-methoxy cinnamate and the like, its presence reinforcing protection afforded by such agents.

Copper lanolate is provided in the form of a turquoise green colored powder which is soluble in oils, fatty bodies and various solvents such as lower alcohols, but insoluble in water. Copper lanolate possesses the following characteristics:

Total acidity: 1—2.6 meq/g;
Lanolate graft: 1—3.5 meq/g;
Residual acidity: <0.80 meq/g; and
Amount of copper: <7.26%

Lanolic acid, an initial reactant in the preparation of copper lanolate, is produced by hydrolysis of lanolin and is provided in the form of a sufficiently complex mixture of fatty acids, among which appear more particularly aliphatic acids, substituted or not, as well as hydroxylated acids.

In accordance with certain studies which have been carried out on this acid, this acid is constituted from about 32 different compounds (see the article of J. Thewlis "Lanolin Fatty Acids and Derivatives" published in American Perfumer and Cosmetics, Vol. 86, August 1971, pages 39-44).

Starting with lanolic acid, the preparation of copper lanolate can be carried out by two different methods:

(1) by double decomposition method which consists in producing initially the sodium or potassium salt of lanolic acid, at a dilution such that it is in isotropic solution, and then by precipitating from this solution copper lanolate by the addition of a solution of a mineral copper salt, for example, copper chloride.

According to this method the reaction temperature is generally between 80° and 100° C. preferably between 90° and 95° C., or (2) by direct reaction of copper hydroxide with lanolic acid.

In accordance with the present invention, the double decomposition method is generally preferred since it leads to satisfactory yields of copper lanolate.

This double decomposition reaction can be schematically represented as follows:

wherein R is the alkyl radical of lanolic acid.

The present invention thus relates to a composition, principally anti-acne composition, containing copper lanolate as the active principle.

In these compositions the concentration of copper lanolate is generally between 0.2 and 50 weight percent, preferably between 1 and 8 weight percent, based on the total weight of the composition.

These compositions can be provided in various forms suitable for a topical application to the skin and principally in the form of lotions, ointments, tinctures, creams, gels, sticks or in aerosol form.

The lotions are aqueous or hydroalcoholic preparations which can also contain certain suspension or dispersion agents, such as cellulose derivatives, gelatin and gums, as well as glycerine or propylene glycol.

The tinctures are alcoholic or hydroalcoholic solutions prepared from an alcohol such as ethanol or isopropanol.

The gels are semi-solid preparations prepared by gelling a solution or suspension of copper lanolate using a gelling agent, such as "Bentone Gel" sold by Société NL Industries for a fatty phase, or a crosslinked polyacrylic acid, for an aqueous phase, such as that sold by Goodrich under the name CARBOPOL, and employed in neutralized form.

According to a preferred embodiment, the compositions according to the present invention are provided in the form of a cream, that is to say, in the form of an emulsion of the water-in-oil or oil-in-water type.

More particularly, the emulsion is provided in the form of a water-in-oil type emulsion, the copper lanolate providing certain emulsifying characteristics when it is combined with a co-emulsifier such as lanolin alcohol and/or hydrogenated lanolin and/or a polyglycerol ester and a dimerized soy oil, such as, for example, the product sold by Société Grinsted under the tradename "HOMODAN PT".

By "hydrogenated lanolin" is meant the mixture of alcohols obtained by catalytic hydrogenation of lanolin, which is essentially composed of esters.

By "lanolin alcohol" is meant the alcohols obtained by hydrolysis of the esters constituting lanolin.

In creams, in the form of a water-in-oil emulsion, wherein copper lanolate is used both as an active compound and as an emulsifier, the weight ratio of copper lanolate to co-emulsifier, mentioned above, is between 90:10 and 10:90 and preferably about 40:60.

The weight ratio of the oil phase to the water phase is generally between 95:5 to 25:75, but preferably in the order of 50:50.

Representative different oils which can usefully be employed as the oil phase include:

(a) animal oils, such as horse oil, hog oil and lanolin, (b) vegetable oils, such as sweet almond oil, avocado oil, ricin oil, olive oil, grape seed oil, poppy oil, colza oil, peanut oil, corn oil, hazelnut oil, jojoba oil, safflower oil and wheat germ oil, (c) hydrocarbon oils, such as paraffin oil, Purcellin oil, perhydrosqualene and solutions of microcrystalline wax in oils, (d) mineral oils, and principally oils whose initial distillation point under atmospheric pressure is about 250° C. and whose final distillation point is about 410° C., and (e) silicone oils, soluble in other oils.

Certain synthetic products such as, for example, saturated esters and principally isopropyl palmitate, isopropyl myristate, butyl myristate, cetyl myristate, hexadecyl stearate, ethyl palmitate as well as the triglycerides of octanoic or decanoic acids and cetyl ricinoleate can also be included in the composition of the present invention.

The oil phase of the emulsions can also contain certain waxes and principally carnauba wax, bees wax, ozokerite and candellila wax.

In order to reinforce the anti-acne activity of copper lanolate, it is possible to use, in accordance with the present invention, certain antibiotics such as the tetracyclines as, for example, chlortetracycline or oxytetracycline or macrolides such as, for example, erythromycine, aminosides such as neomycine, sulfamides (sulfanilamides), synergistins, A. B. polypeptides or chloramphenicol.

Moreover, with the view of improving the skin penetration characteristics of copper lanolate, the compositions according to the present invention can also contain a keratolytic agent, such as benzoyl peroxide, salicylic acid or resorcinol.

The stability of the W/O emulsions can also be improved by complexing the free copper ions. To this effect it has been noted that excellent results are obtained when egg or soy lecithin is employed in an amount ranging up to 5 weight percent, and preferably between 1 and 1.5 weight percent, either alone, or in combination with the tetrasodium salt of ethylene diamine tetraacetic acid in an amount up to 5 weight percent relative to the total weight of the composition.

The use of lecithin in the compositions according to the present invention has proven to be of particular interest particularly where its presence permits self-protection of the composition, that is to say, that in this case it is not necessary to use an extraneous preservative agent.

On the other hand, when lecithin is combined with the tetrasodium salt of ethylene diamine tetra acetic acid (tetra sodium EDTA) or when copper lanolate is employed alone, it is desirable to employ a preservative agent so as to improve the preservation of the composition over prolonged periods of time.

It has also been noted that the anti-acne activity of the compositions of the present invention is very clearly improved when copper lanolate is combined with lecithin and tetrasodium EDTA.

Representative preservative agents, usefully employed in the compositions of the present invention, include, without limitation, methyl parahydroxybenzoate, propyl parahydroxybenzoate and "GERMAL 115", sold by Sutton Labs which is an imidazoline/urea copolymer.

The creams according to the present invention can also be provided in the form of an oil-in-water emulsion. However, in this case the presence of an emulsifying agent is necessary.

As an emulsifying agent for this type of emulsion there can be employed an emulsifying agent or a mixture of emulsifying agents such that the average total HLB is between 10 and 15. For example, a mixture of triethanolamine stearate and oxyethylenated stearic acid, oleyl alcohol oxyethylenated with 10 moles of ethylene oxide and glycerol monostearate can be employed.

In these oil-in-water type emulsions, the emulsifying agent is generally present in an amount between 1 and 12 weight percent, based on the total weight of the composition.

The oil phase in these oil-in-water emulsions is obtained using the same oils and waxes that are generally used for the above described water-in-oil type emulsions.

According to this embodiment of the invention the weight ratio of the water phase to the oil phase in the oil-in-water emulsions is generally between 95:5 and 30:70, and preferably about 70:30.

The compositions according to the present invention can also contain other components such as preservatives, perfumes, dyes, sun screen agents, pigments, humectants, charges such as talc, nylon powder, starch, polyethylene powder and the like.

According to a particular embodiment of the invention, the composition contains, in combination, copper lanolate and a conventional sun screen agent such as, for example, benzylidene camphor, 2-ethyl hexyl p-methoxy cinnamate and the like.

The treatment of acne using the compositions of the present invention comprises applying 2 to 3 times per day a sufficient amount of the composition on the areas of the skin to be treated and this for a period of time ranging from one to four weeks.

The compositions of the present invention can also be employed as a preventative measure, i.e. it can be applied to an area of the skin susceptible of being attacked by acne thereby inhibiting the appearance of pustules, pimples or blackheads.

The following non-limiting examples illustrate a process for the preparation of copper lanolate as well as several anti-acne compositions.

PREPARATION OF COPPER LANOLATE

In a 500 ml reactor there are introduced 46.5 g of lanolic acid, sold by Croda (acid index—137.8), and 100 g of distilled water.

The mixture is heated to boiling and there is then slowly introduced a solution containing 6.4 g of potassium in 30 g of distilled water. The resulting mixture is left to react for one half hour at 90°–95° C. at which point there is slowly introduced, with agitation, a solution of 9.75 g of copper chloride in 30 g of distilled water.

After permitting this mixture to react for about one half hour, while maintaining the temperature at 90°–95° C., the reaction mixture is cooled to 40° C. The resulting precipitate is filtered and washed until the wash solution is no longer cloudy to a silver nitrate test. The precipitate is then dried in an oven under a vacuum.

The expected copper lanolate is thus produced in a yield of 80%, the amount of residual KCl being from 0.6 to 4.5%.

EXAMPLES OF ANTI-ACNE COMPOSITIONS

EXAMPLE 1

There is prepared in accordance with the present invention an anti-acne hydrating cream in the form of a water-in-oil emulsion by admixing the following components:

| | |
|---|---|
| Copper lanolate | 4 g |
| Lanolin alcohol | 6 g |
| Paraffin oil | 27.5 g |
| Petrolatum | 7 g |
| "Bentone Gel" | 4 g |
| Lecithin | 1 g |
| Methyl parahydroxybenzoate | 0.1 g |
| Tetrasodium EDTA | 0.5 g |
| Water, sufficient amount for | 100 g |

EXAMPLE 2

An anti-acne hydrating cream in the form of a water-in-oil emulsion is prepared by admixing the following components:

| | |
|---|---|
| Copper lanolate | 4 g |
| Lanolin alcohol | 6 g |
| Mineral oil | 30 g |
| Ozokerite | 2 g |
| Petrolatum | 8 g |
| Lecithin | 1.5 g |
| Water, sufficient amount for | 100 g |

EXAMPLE 3

An anti-acne composition, in stick form, is prepared by admixing the following components:

| | |
|---|---|
| Copper lanolate | 6 g |
| Lanolin alcohol | 2 g |
| Hydrogenated lanolin | 4 g |
| Isopropyl palmitate | 5 g |
| Candellila wax | 4 g |
| Oxokerite | 20 g |
| Lanolin | 10 g |
| Paraffin oil | 48.5 g |
| Methyl para hydroxybenzoate | 0.1 g |
| Water | 4.9 g |

EXAMPLE 4

A facial anti-acne composition, in stick form, is prepared by admixing the following components:

| | |
|---|---|
| Copper lanolate | 3.8 g |
| Hydrogenated lanolin | 5.7 g |
| Ozokerite | 15 g |
| Isopropyl palmitate | 10 g |
| Paraffin oil | 13.5 g |
| Iron oxide | 1 g |
| Titanium oxide | 1 g |
| Methyl parahydroxybenzoate | 0.3 g |
| Tetrasodium EDTA | 1 g |
| Water, sufficient amount for | 100 g |

EXAMPLE 5

There is prepared, in accordance with the present invention, an anhydrous anti-acne gel composition by admixing the following components:

| | |
|---|---|
| Petrolatum | 13 g |
| Copper lanolate | 2 g |
| Paraffin oil | 34.7 g |
| Isopropyl palmitate | 37 g |
| Ozokerite | 10 g |
| "Bentone Gel" | 3 g |
| Propyl parahydroxybenzoate | 0.3 g |

EXAMPLE 6

In accordance with the present invention an anti-acne cream in the form of an oil-in-water emulsion is prepared by admixing the following components:

| | |
|---|---|
| Copper lanolate | 1 g |
| Petrolatum oil | 0.5 g |
| Glycerol monostearate | 1.9 g |

| -continued | |
|---|---|
| Stearin | 1 g |
| Hydrin | 3 g |
| Butylhydroxytoluene | 0.006 g |
| Perhydrosqualene | 17 g |
| Hazelnut oil | 5 g |
| Triethanolamine | 0.75 g |
| Crosslinked polyacrylic acid (CARBOPOL) | 0.25 g |
| Preservative agent | 0.3 g |
| Propylene Glycol | 3 g |
| Perfume | 0.8 g |
| Demineralized water, sufficient amount for | 100 g |

EXAMPLE 7

An anti-acne ointment is prepared by admixing the following components:

| | |
|---|---|
| Copper lanolate | 35 g |
| Petrolatum | 32 g |
| Sweet almond oil | 32.7 g |
| Propyl parahydroxybenzoate | 0.3 g |

EXAMPLE 8

In accordance with the present invention an anti-acne lotion is prepared by admixing the following components:

| | |
|---|---|
| Copper lanolate | 0.5 g |
| Ethyl alcohol | 9.5 g |
| Propylene glycol | 40 g |
| Glycerine | 40 g |
| Crosslinked polyacrylic acid (CARBOPOL) | 0.25 g |
| Perfume | 0.5 g |
| Preservative | 0.5 g |
| Water, sufficient amount for | 100 g |

EXAMPLE 9

An anti-solar and anti-acne composition in stick form is prepared by admixing the following components:

| | |
|---|---|
| Cocoa butter | 5 g |
| Ozakerite | 10 g |
| Copper lanolate | 5 g |
| Petrolatum | 8 g |
| Turnsole oil | 12 g |
| Lanolin | 12 g |
| 2-ethyl hexyl p-methoxy cinnamate | 5 g |
| Titanium oxide | 1 g |
| Polyethylene powder | 1 g |
| Butyl hydroxyanisole | 0.03 g |
| Perfume | 0.8 g |
| Petrolatum oil, Codex, sufficient amount for | 100 g |

EXAMPLE 10

In accordance with the invention a sun screen and anti-acne cream for dry skin, having an average index of sun screen protection, is prepared by admixing the following components:

| | |
|---|---|
| Magnesium lanolate | 4 g |
| Hydrogenated lanolin | 5 g |

| -continued | |
|---|---|
| Copper lanolate | 2.5 g |
| Petrolatum | 20 g |
| Glyceryl lanolate | 3 g |
| Cholesterol | 0.3 g |
| Lanolin | 2 g |
| Isopropyl palmitate | 3 g |
| Petrolatum oil, Codex | 10 g |
| 2-ethylhexyl p-methoxy cinnamate | 3 g |
| Benzylidene camphor | 2 g |
| Butyl parahydroxybenzoate | 0.4 g |
| Perfume | 0.8 g |
| Demineralized water, sufficient amount for | 100 g |

What is claimed is:

1. Copper lanolate.

2. Copper lanolate produced by initially preparing a sodium or potassium salt of lanolic acid at a dilution such that said salt is in isotropic solution and then precipitating said copper lanolate from said solution by the addition thereto of a solution of a copper salt, said copper lanolate being soluble in oils, fatty bodies and lower alcohols but insoluble in water and having the following characteristics: total acidity—1 to 2.6 meq/g, grafted lanolate—1 to 3.5 meq/g, residual acidity—<0.08 meq/g, and amount of copper—<7.26 percent.

3. A anti-acne composition for application to the skin comprising, in a cosmetically acceptable vehicle or carrier, copper lanolate in an amount ranging from 0.2 to 50 weight percent based on the total weight of said composition.

4. The composition of claim 3 wherein said copper lanolate is present in an amount ranging from 1 to 8 weight percent.

5. The composition of claim 3 wherein said cosmetically acceptable vehicle or carrier is a water-in-oil emulsion, wherein copper lanolate comprises an emulsifier in combination with a co-emulsifier selected from lanolin, hydrogenated lanolin, a polyglycerol ester or dimerized soy oil, or a mixture thereof.

6. The composition of claim 5 wherein the weight ratio of copper lanolate to said co-emulsifier ranges from 80:20 to 10:90.

7. The composition of claim 5 wherein the weight ratio of copper lanolate to said co-emulsifier is about 40:60.

8. The composition of claim 5 wherein the weight ratio of the oil phase to the water phase of said water-in-oil emulsion ranges from 95:5 to 25:75.

9. The composition of claim 5 wherein the weight ratio of the oil phase to the water phase of said water-in-oil emulsion is about 50:50.

10. The composition of claim 3 which also includes egg lecithin or soy lecithin in an amount up to 5 weight percent based on the total weight of said composition.

11. The composition of claim 3 which also includes egg lecithin or soy lecithin in an amount ranging from 1 to 1.5 weight percent based on the total weight of said composition.

12. The composition of claim 3 which also includes the tetrasodium salt of ethylene diamine tetraacetic acid in an amount up to 5 weight percent based on the total weight of said composition.

13. The composition of claim 3 wherein said cosmetically acceptable vehicle or carrier is an oil-in-water emulsion, said emulsion containing an emulsifying agent having a total average HLB between 10 and 15 and being present in an amount ranging from 1 to 12 weight percent based on the total weight of said composition.

14. The composition of claim 13 wherein the weight ratio of the water phase to the oil phase of said oil-in-water emulsion ranges from 95:5 to 30:70.

15. The composition of claim 13 wherein the weight ratio of the water phase to the oil phase of said oil-in-water emulsion is about 70:30.

16. The composition of claim 3 which also contains an effective amount of a keratolytic agent.

17. The composition of claim 16 wherein said keratolytic agent is benzoyl peroxide, salicylic acid or resorcinol.

18. The composition of claim 3 which also includes an effective amount of a sun screen agent.

19. The composition of claim 18 wherein said sun screen agent is benzylidene camphor or 2-ethyl hexyl p-methoxy cinnamate.

* * * * *